(12) United States Patent
Paton et al.

(10) Patent No.: US 7,025,764 B2
(45) Date of Patent: Apr. 11, 2006

(54) BONDING OF SOFT BIOLOGICAL TISSUES BY PASSING HIGH FREQUENCY ELECTRIC CURRENT THERETHROUGH

(75) Inventors: Boris E. Paton, Kiev (UA); Vladimir K. Lebedev, Kiev (UA); David S. Vorona, Kiev (UA); Volodimir I. Karchemsky, Kiev (UA); Yuri A. Furmanov, Kiev (UA); Alexsey V. Lebedev, Kiev (UA); Valery A. Vasilchenko, Kiev (UA); Dmitry F. Sidorenko, Kiev (UA); Vitaly P. Iemchenko-Ribko, Kiev (UA); Olga N. Ivanova, Kiev (UA); Alexandr Y. Furmanov, Kiev (UA); Yevgen V. Zhyvodernikov, Kiev (UA); Andrei A. Lyashenko, Kiev (UA); Irina M. Savitskaya, Kiev (UA)

(73) Assignee: Live Tissue Connect, Inc., Corpus Christi, TX (US)

( * ) Notice: Subject to any disclaimer, the term of this patent is extended or adjusted under 35 U.S.C. 154(b) by 197 days.

(21) Appl. No.: 10/310,203

(22) Filed: Dec. 4, 2002

(65) Prior Publication Data

US 2003/0114845 A1 Jun. 19, 2003

Related U.S. Application Data

(62) Division of application No. 09/022,869, filed on Feb. 12, 1998, now Pat. No. 6,562,037.

(51) Int. Cl.
*A61B 18/18* (2006.01)

(52) U.S. Cl. .......................................... 606/34; 606/42

(58) Field of Classification Search ............. 606/32–34, 606/37–52
See application file for complete search history.

(56) References Cited

U.S. PATENT DOCUMENTS

| 3,980,085 A | 9/1976 | Ikuno |
| 4,154,240 A | 5/1979 | Ikuno et al. |

(Continued)

FOREIGN PATENT DOCUMENTS

| DE | 196 41 563 A1 | 4/1998 |
| EP | 0 703 461 A1 | 9/1995 |

(Continued)

OTHER PUBLICATIONS

"Automatically controlled bipolar electrocoagulation" by Vallfors and Bergdahi, Neurosurgery Rev. 7 (1984), pp. 187–190.

"The mechanism of Blood Vessel Closure by High Frequency Electrocoagulation" by Sigel et al, Surgery Gynecology & Obstetrics, pp. 823–831, Oct. 1965.

(Continued)

*Primary Examiner*—Rosiland Rollins
(74) *Attorney, Agent, or Firm*—Charles W. Hanor, P.C.

(57) ABSTRACT

Technique for bonding soft biological tissue having an incision therein with forceps adapted to grip a portion of tissue on both sides of incision. Electrodes are secured to forceps for contracting the tissue portion. An electrical power source provides a high frequency electrical signal to electrodes to be passed through the tissue portion. The electrical power source is controlled to provide electrodes with one voltage signal during a first of two stages, wherein the voltage rises linearly, and another voltage signal during a second of the two stages, wherein the voltage is stabilized and modulated with a low frequency rectangular signal. A clamping means applies force with the forceps to compress the tissue at one or different levels during two time periods while the high frequency voltage is passed through the electrodes. The tissue impedance is measured as a function of time, with its minimal value being determined and stored.

9 Claims, 9 Drawing Sheets

U.S. PATENT DOCUMENTS

| | | |
|---|---|---|
| 4,418,692 A | 12/1983 | Guay |
| 4,471,787 A | 9/1984 | Bentall |
| 4,492,231 A | 1/1985 | Auth |
| 4,556,051 A | 12/1985 | Maurer |
| 4,633,870 A | 1/1987 | Sauer |
| 4,738,250 A | 4/1988 | Fulkerson et al. |
| 4,892,098 A | 1/1990 | Sauer |
| 4,944,746 A * | 7/1990 | Iwata et al. ............ 606/195 |
| 5,151,102 A | 9/1992 | Kimayama et al. |
| 5,158,081 A | 10/1992 | McWhorter et al. |
| 5,190,541 A | 3/1993 | Abele et al. |
| 5,300,065 A | 4/1994 | Anderson |
| 5,336,221 A | 8/1994 | Anderson |
| 5,342,381 A | 8/1994 | Tidemand |
| 5,342,393 A | 8/1994 | Stack |
| 5,364,389 A | 11/1994 | Anderson |
| 5,403,312 A | 4/1995 | Yates et al. |
| 5,415,657 A | 5/1995 | Taymor-Luria |
| 5,423,814 A | 6/1995 | Zhu et al. |
| 5,431,645 A | 7/1995 | Smith et al. |
| 5,443,463 A | 8/1995 | Stern et al. |
| 5,450,845 A | 9/1995 | Axelgaard |
| 5,476,481 A | 12/1995 | Schondorf |
| 5,496,312 A | 3/1996 | Klicek |
| 5,507,744 A | 4/1996 | Tay et al. |
| 5,540,684 A | 7/1996 | Hassler, Jr. |
| 5,558,671 A | 9/1996 | Yates |
| 5,562,503 A | 10/1996 | Ellman et al. |
| 5,713,896 A | 2/1998 | Nardella |
| 5,718,701 A | 2/1998 | Shai et al. |
| 5,776,130 A | 7/1998 | Buysse et al. |
| 5,817,093 A | 10/1998 | Williamson, IV et al. |
| 5,827,271 A | 10/1998 | Buysse et al. |
| 5,954,686 A | 9/1999 | Garito et al. |
| 6,086,585 A * | 7/2000 | Hovda et al. ............ 606/45 |
| 6,086,586 A | 7/2000 | Hooven |
| 6,228,080 B1 | 5/2001 | Gines |
| 6,245,065 B1 | 6/2001 | Panescu et al. |
| 6,402,741 B1 * | 6/2002 | Keppel et al. ............ 606/34 |

FOREIGN PATENT DOCUMENTS

| | | |
|---|---|---|
| EP | 0 761 174 A1 | 9/1996 |
| WO | WO 97/10764 | 8/1996 |
| WO | WO 98/38935 | 3/1998 |

OTHER PUBLICATIONS

Bergdahl B., Vallfors B. "Studies on coagulation and the development of an automatic computerized bipolar coagulator." Journal of Neurosurgery Jul. 1991; 75(1): 148–51 (Abstract only).

* cited by examiner

BONDING OF SOFT BIOLOGICAL TISSUES BY PASSING HIGH FREQUENCY ELECTRIC CURRENT THERETHROUGH

This application is a Divisional of Ser. No. 09/022,869 filed Feb. 12, 1998 now U.S. Pat. No. 6,562,037.

BACKGROUND OF THE INVENTION

The present invention is directed to a technique for bonding soft biological tissue to close an incision therein and, in particular, to heating of the tissue with high frequency electric current in combination with compression of the tissue.

For purposes of the ensuing discussion, soft biological tissue will be referred to just by the term "tissue" for reasons of simplicity and economy of space, and should be understood to mean any tissue other than bone, such as skin, organs, blood vessels and nerves. When tissue is injured, it must be repaired by re-joining the edges of tissue that has been torn or cut. For example, when tissue is cut during a surgical operation, the incision(s) must be closed to complete the surgery. In fact, a tissue break (particularly in blood vessels) may also need to be closed even during surgery, such as to provide hemostasis, namely to control bleeding. Every cut, puncture or break in tissue due to any reason is referred to herein generically as an "incision".

Many techniques are known for closing an incision. Some of these techniques are suturing, clamping, stapling and gluing. These techniques have a number of well known disadvantages which include one or more of the following: leaving a foreign body in the tissue, pinching of tissue which can cause delayed healing and/or inflammation, allergic reaction, limited applicability, complexity of use, and the need for expensive equipment.

Other techniques of connecting blood vessels use laser radiation, heated tools and the passing of high frequency current directly through the parts of tissue being connected. All the above mentioned methods employ the phenomenon of tissue albumen denaturation caused by heating. When the temperature exceeds 55° C. the denaturation causes albumen coagulation. The globular molecules of albumen become straightened and entangled among themselves. If two edges of tissue are connected and heated the entanglement of albumen molecules results in their bonding. The higher the temperature, the faster and better is the coagulation. However, at temperature exceeding 100° C. the tissue becomes dehydrated, its electric resistance increases, which leads to further temperature rise and charring of the tissue.

Quite a number of research efforts have been published on laser techniques in blood vessel surgery. Still this technique has not been accepted for general clinical use because of the technical complexity of its utilization and because of inadequate surface energy release. As to employment of high frequency current for heating tissue, the technique is widely used in surgery for hemostasis.

In tissue bonding, as with suturing for example, the separated tissue edges must be rejoined to facilitate healing. The joint should be relatively strong, it must promote healing and minimize if not eliminate any problem which interferes with healing. However, the use of the existing bipolar devices for connecting soft tissues other than walls of compressed blood vessels encounters insurmountable difficulties. Specifically, it has been difficult to correctly set the electrical signal parameters to achieve such aims. This is due, at least in part, to the fact that tissue has an electrical resistance which can vary widely depending on many factors such as tissue structure and thickness as well as the tool/tissue contact area which is not controlled in any way. If too little current is applied, then the tissue joint can be spongy, weak and unreliable. On the other hand, if too much current is applied, then the working surface of the electrode can stick to the tissue so that removal of the electrode causes bleeding and possible injury. Also, the tissue in the overly-heated zone can become desiccated and charred. Therefore, such high frequency coagulative devices have seen limited use for only hemostasis of blood vessels of relatively small diameter. These devices have not been used for replacing the well known above-mentioned means for bonding tissue ("bonding" is used in the sense of closing incisions to facilitate healing), such as suturing, stapling, etc. even though their use is not subject to the above-mentioned disadvantages of such means for bonding tissue.

Two types of tools are used for high frequency electrocoagulation, namely mono-polar and bipolar. The discussion below will be limited solely to bipolar devices which provide an electric current flow within the tissue volume clamped between the electrodes.

Use of bipolar devices to close incisions in tissue which must be healed will be appreciated as presenting quite a challenging task because the amount of damaged tissue, such as due to charring or other healing-delaying effects, must be minimal and not very deep, and "overcoagulation" must be avoided. Prior art techniques have been proposed to determine the degree of coagulation based on the electrical impedance of the tissue. The relationship between electrical tissue impedance over time and coagulation is described in the article "Automatically controlled bipolar electrocoagulation" by Vallfors and Bergdahl, Neurosurgery Rev. 7 (1984), pp. 187–190. As energy is applied to the tissue, the impedance decreases until it reaches a minimum value. If current continues to be applied, the authors describe imprecisely that the tissue begins to dry out due to the heat generated therein, and the impedance rises. Unless the heating is stopped, severe tissue damage will occur. Thus, the Vallfors and Bergdahl technique provides for determination of the instant of occurrence of the impedance minimum and then stops the current flow a preset time thereafter. U.S. Pat. No. 5,403,312 also utilizes this phenomenon to monitor the impedance, change in impedance and/or the rate of change in impedance to determine whether it is within a normal range. However, these techniques are typically applied to blood vessel coagulation. Usage of these techniques for other types of tissue creates severe difficulties due to the wide variation in values of impedance which can be encountered due to, for example, tissue structure, thickness, condition of the tissue and condition of the tool surface.

SUMMARY OF THE INVENTION

One object of the present invention is to provide an improved bipolar electrocoagulation technique for bonding tissue with heat energy created by high frequency electrical current passed therethrough between electrodes.

Another object of the invention is to prevent sticking of the electrodes to the tissue.

A further object of the invention is to achieve a stronger bond.

Yet another object of the invention is to prevent burning of tissue in the bipolar electrode zone.

One other object of the invention is to provide a consistently good tissue bond regardless of differences in tissue structure and thickness.

Still another object of the invention is to bond tissue to close an incision quickly and reliably.

Another object of the invention is to bond tissue in a way which promotes fast healing.

A further object of the invention is to rely on measurement of tissue impedance to accurately control the degree of coagulation which bonds the tissue for a wide variety of different tissues.

Yet another object of the invention is to design the electrodes such that they can function as an effective heat sink for the heated tissue with which they are in contact. Another object of the invention is to design the electrodes to maintain uniformity in the area of electrode/tissue contact.

These and other objects are attained in accordance with one aspect of the present invention directed to a method and apparatus for bonding soft biological tissue having an incision therein with forceps adapted to grip a portion of the tissue on both sides of the incision. Electrodes are provided for contacting the tissue portion. An electrical power source provides a high frequency electrical signal to the electrodes to be passed through the tissue portion, and the electrical power source is controlled to provide the electrodes with one voltage signal during a first of two stages, and another voltage signal during a second of the two stages.

Another aspect of the present invention is directed to a method and apparatus for bonding soft biological tissue having an incision therein with forceps adapted to grip a portion of the tissue on both sides of the incision. Electrodes are provided for contacting the tissue portion. An electrical power source provides a high frequency electrical signal to the electrodes to be passed through the tissue portion, and a clamping means applies force with the forceps to compress the tissue portion, such force being set to different levels in two time periods, respectively, while the high frequency electrical signal is being passed through the tissue portion.

Another aspect of the present invention is directed to a method and apparatus for bonding soft biological tissue having an incision therein with forceps adapted to grip a portion of the tissue on both sides of the incision. Electrodes are provided for contacting the tissue portion. An electrical power source provides a high frequency electrical signal to the electrodes to be passed through the tissue portion, with a constant voltage level of the signal being provided during at least a portion of a time period when the high frequency electrical energy is passed through the tissue portion, and the constant level being modulated by a low frequency signal.

Another aspect of the present invention is directed to a method and apparatus for bonding soft biological tissue having an incision therein with forceps adapted to grip a portion of the tissue on both sides of the incision. Electrodes are provided for contacting the tissue portion. An electrical power source provides a high frequency electrical signal to the electrodes to be passed through the tissue portion. The electrodes are dimensioned relative to size of the tissue portion to be an effective heat sink for conducting heat away from the tissue and thereby prevent sticking of tissue to the electrodes.

Another aspect of the present invention is directed to a method and apparatus for bonding soft biological tissue having an incision therein with forceps adapted to grip a portion of the tissue on both sides of the incision. Electrodes are provided for contacting the tissue portion. An electrical power source provides an electrical signal to the electrodes to be passed through the tissue portion. The impedance variation in the tissue portion as a function of time, while the electrical signal passes through the tissue portion, is predetermined to provide a preselected impedance value. The impedance is measured to provide a measured impedance signal as a function of time, while the electrical signal passes through the tissue portion, and the electrical signal is stopped from being passed through the tissue portion when a value of the measured impedance signal reaches a preset impedance value relative to the preselected impedance value, with the preselected impedance value being specific in particular to the biological tissue being bonded.

Another aspect of the invention is directed to a method and apparatus for bonding soft biological tissue having an incision therein with forceps adapted to grip a portion of the tissue on both sides of the incision. Electrodes are provided which are adapted to contact the tissue portion in an electrode/tissue contact area. An electrical power source provides a high frequency electrical signal to the electrodes to be passed through the tissue portion. The electrodes are dimensioned relative to size of the tissue portion to maintain uniformity in the electrode/tissue contact area.

DETAILED DESCRIPTION OF THE PREFERRED EMBODIMENTS

Figure 1:
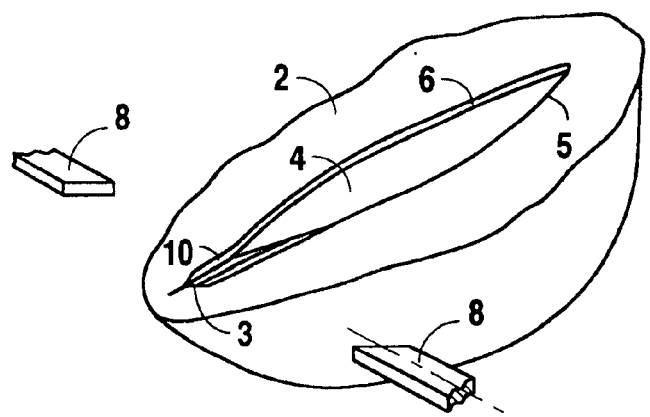
FIG. 1 is a perspective view of a section of soft biological tissue with an incision therein prior to performing tissue bonding.

FIG. 1 shows tissue 2 with an incision 4 formed therein. Incision 4 could have been formed as part of some surgery done on a patient, or it could be an injury due to some type of trauma. The incision can be a cut in the skin or in a wall of an organ, or the organ itself, e.g. a blood vessel or nerve. In any case, the incision must be closed by bonding, or joining, the edges of tissue 5 and 6 on either side of the incision to each other.

Figure 2:
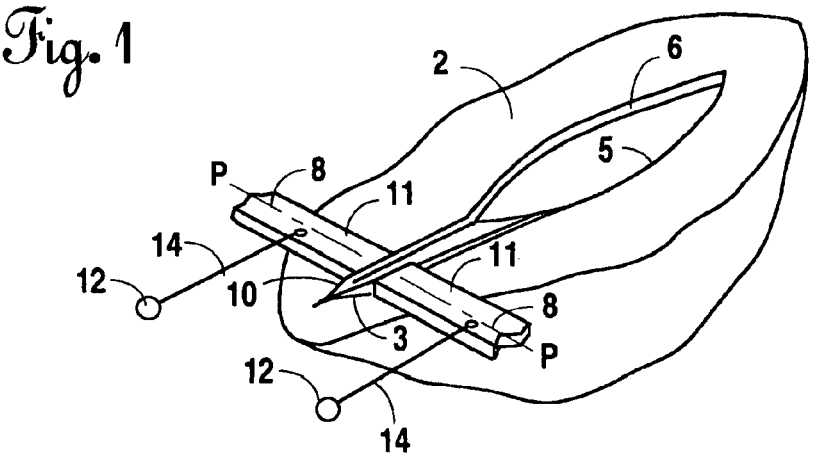
FIG. 2 shows the perspective view of FIG. 1 with tissue on both sides of the incision being compressed between two electrodes to form a grasped flange of tissue in accordance with a first embodiment of the invention.

In accordance with the present invention, the edges 5, 6 at end 3 of the incision are gripped and raised by pincers (not shown) to form tissue portion 10 in the form of a flange. This is depicted in FIG. 1. A forceps tool (referred to herein as a forceps) is provided in the form of any instrument capable of gripping the tissue and selectively adding a clamping force under manual control. Various forceps designs are well known. Typically they include a pair of arms with opposed ends between which the tissue can be gripped. Forceps arranged in accordance with the invention are described below. For now it is sufficient to know that the forceps include clamp arms 8. As shown in FIG. 2, electrodes 11 are secured at the opposed ends of clamp arms 8 to grip portion 10 of the tissue therebetween. To grip the tissue, sufficient force is used to just retain the tissue between electrodes 11 so that it does not slip out of position. The gripped tissue is not significantly compressed.

Clamp arms 8 are entirely metallic or only the tissue-grasping tip is metallic to form electrodes 11. Thus, the tissue portion, or flange, 10 is in contact with two electrodes 11 on its sides. Current from a high frequency ("HF") electric power source 12 is provided to electrodes 11 by conductor wires 14. This creates a bipolar electrode arrangement so that electric current generated between electrodes 11 passes through flange 10 of tissue 2.

Figure 3:
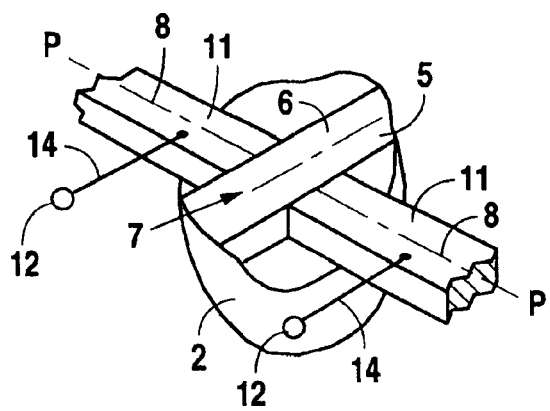
FIG. 3 is an enlarged view of a portion of FIG. 2 prior to passing electric current through the grasped flange of tissue.
Figure 4:
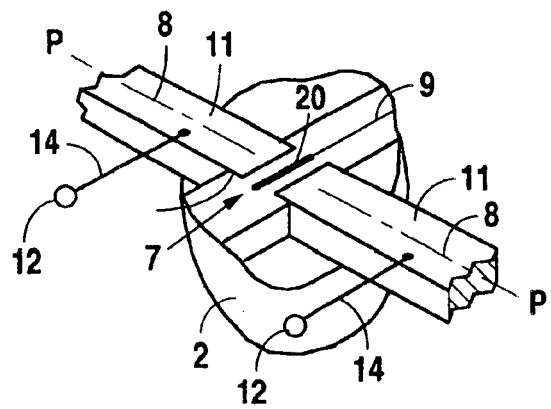
FIG. 4 is similar to the view of FIG. 3, but with the grasped flange of tissue being compressed while electric current is applied to bond the tissue.

Electrodes 11 are initially pressed toward each other to engage flange 10 with a minimal pressure P sufficient to grip flange 10, as explained above. However, the tissue need not yet be compressed to any substantial degree, as shown in FIG. 3. In contrast, by virtue of the extent to which FIG. 4 shows that the electrodes sink into the tissue at portion 16, pressure P has been increased to significantly compress, or clamp, the flange 10. Then, an HF signal is applied to electrodes 11 from source 12.

It must be realized that the zone 7 between the electrodes 11 contains an electrical impedance. It should be noted that heat is generated by current flow through tissue due to its resistance. Therefore, resistance is used below when the invention is explained in terms of heat due to current flow, although it is understood that when measurements are made, the measured parameter is impedance. Tissue resistance has several components. One component, called the tissue/tissue component, is the resistance between the opposed edges 5, 6 of tissue on either side of incision 2. Another component, called the bulk tissue resistance component, is the resistance of that portion of tissue 2 which is grasped between the electrodes 11 in the form of flange 10. A further component, called the electrode/tissue component, is the contact area between the electrodes 11 and the tissue of flange 10.

Tissue between electrodes 11 is heated because of heat generated by electric current flowing through the tissue due to the electric resistance of the tissue in zone 7. Due to the presence of many variables, it is difficult if not impossible to accurately predict the magnitude of the resistance components nor how heat will spread therethrough and be released therefrom.

The edges 5, 6 are preferably clamped with a preset pressure of a certain experimentally determined magnitude depending on tissue structure and thickness, and the bonding current is passed through these clamped edges. One benefit of such clamping (others are presented below) is that it serves to form better contact areas by conforming the opposed surfaces to each other. Rather than having a random number of point contacts between, say, edges 5 and 6, this approach creates a firm surface contact with more predictable electric contact resistances between the electrodes and tissue, and between tissue and tissue. As a result, it stabilizes the heat generated by electric current due to these resistance components. At the same time, the clamping of the tissue edges by a preset pressure during the process of heating allows densification of the straightening and entangling albumin molecules in the tissue/tissue contact area to thereby improve the strength of the bond created with this bipolar heating as compared to what the bond strength would be without such clamping.

One advantage of using alternating current, particularly of high frequency, is as follows. While direct current traverses the tissue edges, electrolytic ions move in the direction of the electric poles in accordance with their polarity. A sufficient concentration of these ions on the locally heated tissue ends may produce an electrolytic effect which causes a chemical burn of the tissue. By using alternating current for heating the tissue edges, the electrolyte ions do not move in the tissue just in one direction but, rather, they change their direction of movement with the changing polarity, so that the ions oscillate about their quiescent state. The amplitude of these oscillations varies inversely with the frequency of alternating current. Thus, a higher frequency of alternating current will result in lower amplitude of these oscillations, thereby reducing the electrolytic effect.

Thus, a strong and effective bond between the tissue edges is achieved by means of first clamping such edges together with a preset pressure having a level depending on tissue structure and thickness, and then passing a high frequency alternating current through these clamped edges sufficient to heat the tissue in the current conductive zone 7.

A further feature aimed at overcoming the above-described drawbacks of bipolar devices, and in accordance with a principal aspect of the present invention, is to apply heat in a two-stage thermal cycle to the tissue being bonded in zone 7. The first stage stabilizes the bulk tissue resistance component. Then, in the second stage, a good bond is created by virtue of being able to provide stable, predictable tissue heating and to produce satisfactory heat removal from the electrode/tissue interface. As explained below, this contributes to creating a defectless and reliable bond while avoiding sticking of the tissue to the electrodes.

It is advisable that pressure P applied to flange 10 by the arms 8 through electrodes 11 does not exceed 15 N/mm$^2$ and be no lower than 0.5 N/mm$^2$. The wide range of pressure values is explained by the fact that soft tissues have widely varying thicknesses and structures (compare, for example, tissues of a nerve, stomach, liver, skin, etc.). The exceeding of the maximal acceptable pressure value P for a particular type of tissue with a certain thickness δ has been experimentally shown to cause a considerable volumetric deformation of tissue in the bonding zone 7 with the result that it increases the time required to heal the tissue after bonding. The decrease of pressure below a minimal acceptable value for a certain type of tissue with a thickness δ leads to deterioration of the joint reliability because of unstable electric resistance components (as discussed above) and heat development, and because insufficient entanglement among albumin molecules is created in the tissue/tissue contact area. It also leads to strong sticking of the contacting surface of the welding electrodes to the tissue surface because of the increased value of electric contact resistances and poorer heat release in the electrode/tissue contact area.

The time duration T during which current is passed through the tissue is within the range of 0.1 to 3.0 seconds depending on tissue thickness and structure. The relation between heating time and tissue thickness is derived from Fourier's Law of Heat Conduction (see B. Paton, V. Lebedev, "Electric equipment for flash-butt welding. Elements of the theory.", Mashinostroyeniye Publishers, Moscow 1969, pages 38–45) in accordance with which a dimensionless number II is a constant value.

$$II = \frac{aT}{\delta^2}$$

where a=λ/c·γ is biological tissue temperature conductivity;
 λ is specific heat conductivity,
 c is heat capacity,
 γ is tissue density, and
 δ is tissue thickness in a compressed state.

Since II is a constant, the heating duration time T should be proportionate to the tissue thickness squared. Exceeding the maximum limiting value of time T for a particular type of tissue with a certain thickness δ is related, as has been experimentally shown, to tissue overheating which slows down the healing process and increases the probability of electrode adhesion to tissue. Decreasing time T below the minimum allowable value leads, as has been experimentally shown, to insufficient coagulation of albumin in the tissue and poorer bond reliability.

As pointed out above, one key aspect of the invention is to apply a two-stage thermal cycle. Thus, time T is divided into portions $T_1$ and $T_2$. During the first stage $T_1$, voltage on the electrodes is raised from a starting value of 0 to a preset maximum level. The selection of the voltage rise rate of the power source is based on prior experience and taking into account the type of tissue and the thickness of tissue. The rate of voltage increase is preferably the same throughout first stage $T_1$ so that it appears as a straight line, or ramp, on a graph of voltage vs. time. The maximum value reached in first stage $T_1$ is preferably the voltage used for second stage $T_2$. During stage $T_2$, the applied voltage is constant.

A rate of voltage rise which is too slow may result in expanding the area of the heated tissue beyond the borders of zone 7 and thereby reduce the heating localization, and this will eventually result in increasing the time required for healing. A rate of voltage rise which is too fast may cause nonuniformity in tissue heating which impairs the stability of bonding formation conditions.

The first stage of the thermal cycle is effective for the thermal and mechanical development of better contact areas and forming a conductive path through which the larger portion of current flows. During this first stage, pressure P is applied to firmly clamp the opposed tissue edges against each other to create surface/surface rather than point/point contact areas.

For the first stage of the thermal cycle, voltage is increased at a given rate during time $T_1$. Then, a steady voltage level is applied for time $T_2$ of the second stage which commences immediately after completion of the first stage. This second stage is the bonding part of the thermal cycle, which provides straightening, interlacing and infiltration of albumin molecules in the current conductive zone 7 (FIG. 3) to reliably bond the edges 5 and 6 clamped (FIG. 4) between electrodes 11.

Good heat transfer is achieved by the first stage because it creates extra contact areas in the current conductive zone 7 which provide fast heat removal of heat due to the electrode/tissue resistance component. This reduces the probability of adherence, or sticking, of the electrode work surface to the tissue edges.

Figure 5:
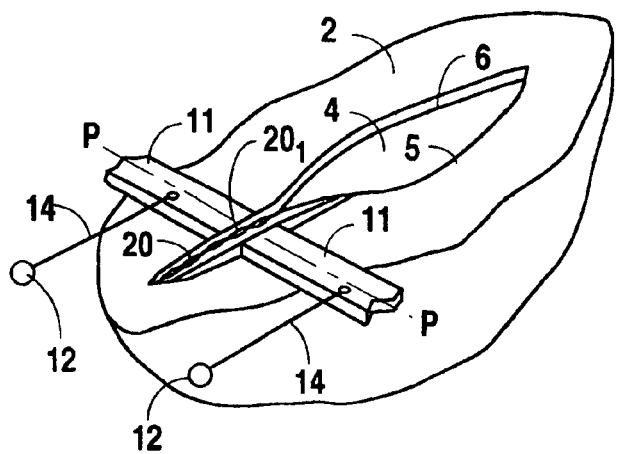
FIG. 5 is similar to the view of FIG. 4, but after the electrodes have made a bond at one spot and then moved to another spot along the incision.
Figure 6:
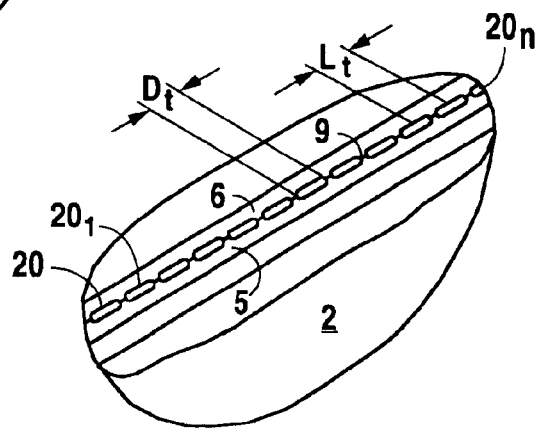
FIG. 6 is an enlarged perspective view of a lap-welded seam formed in bonding the tissue.
Figure 7:
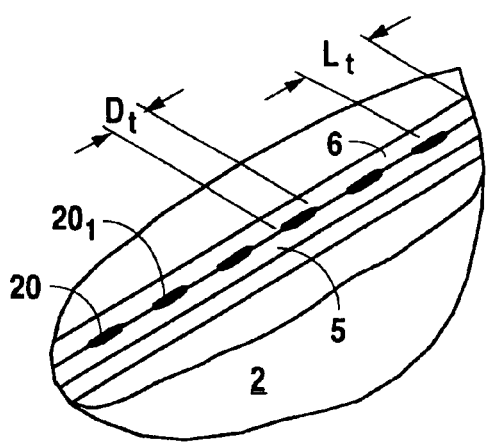
FIG. 7 is similar to the view of FIG. 6, but showing a spot-welded seam.

After bonding of the edges at a first spot 20 (see FIG. 5) along seam 9, the electrodes 11 are returned to their initial, separated position (which is shown in FIG. 1). To make the second and the subsequent bonded spots on the seam 9 of the flanged edges 5 and 6 of tissue 2, the thermal cycle described hereinabove is repeated to produce spots $20_1, 20_2 \ldots 20_n$ (see FIGS. 5–7). If it is necessary to provide a hermetically sealed joint of tissue, step Lt by which electrodes 11 are moved along the seam (FIG. 6) must be selected in such a manner that the previously bonded spot (for instance spot 20) is overlapping the following spot 20 by 10 to 30% of its length Dt (i.e. Lt<Dt). If tight sealing is not required, step Lt (FIG. 7) is selected (i.e. Lt>Dt) in accordance with other requirements (for instance strength, external appearance of the joint, etc.).

Figure 8:
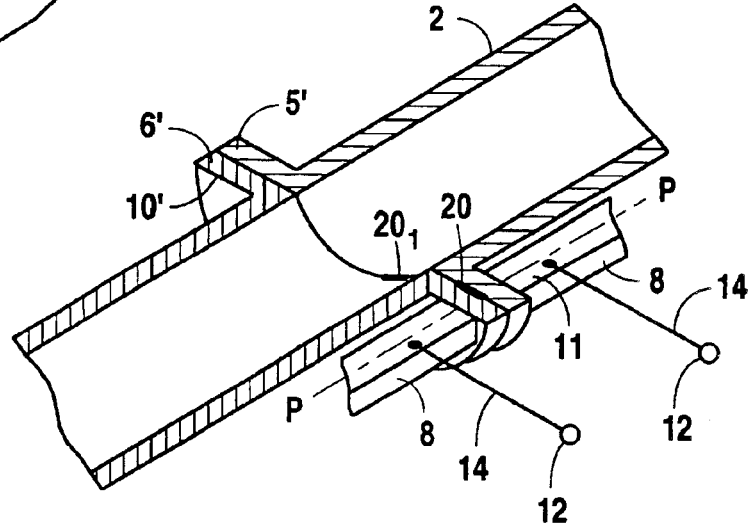
FIG. 8 shows a cross section of a hollow organ with a flanged portion of tissue at the seam being grasped between the electrodes of a second embodiment of the present invention.

FIG. 8 shows a hollow tissue 2, such as a blood vessel, which has been severed. The two ends 5' and 6' are joined to form a circular flange 10', and electrodes 11 at the ends of arms 8 clamp the tissue therebetween at one point along the periphery of flange 10'. As current is passed between the electrodes through the tissue, bond 20 is made at one point along seam 9. Electrodes 11 can then be moved around the periphery to form bond $20_1$, and so on around the entire circumference of circular flange 10'.

Figure 9:
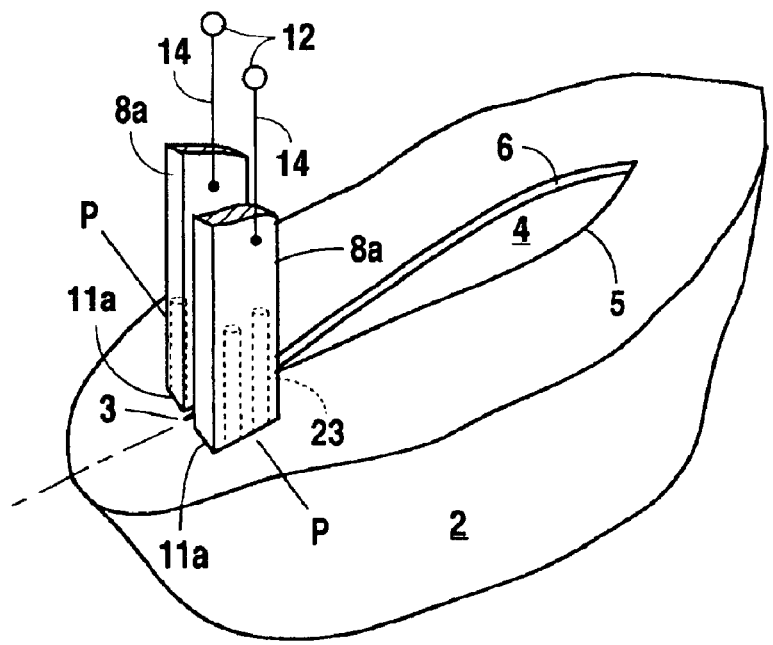
FIG. 9 shows a perspective view of a third embodiment of the invention.

As shown in the embodiment of FIG. 9, clamping arms 8*a* are provided with electrodes 11*a* having holes 23 in the bottom and side which engage the tissue. Electrodes 11*a* are hollow and have a connection (not shown) to a vacuum source (not shown). When vacuum is applied to electrodes 11*a* they grip the tissue so that it can be held securely and properly positioned for having current pass effectively therethrough to carry out the above-described thermal cycle.

Figure 10:
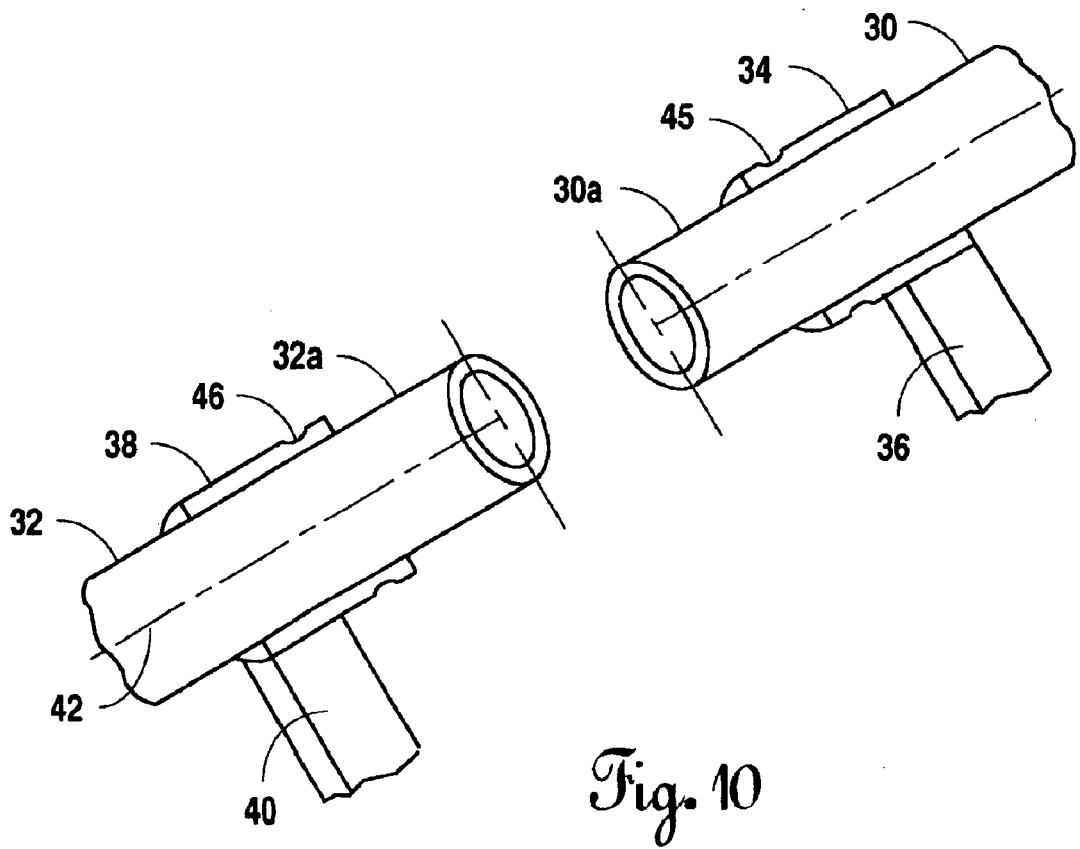
FIGS. 10–12 are perspective views of a fourth embodiment of the invention.
Figure 11:
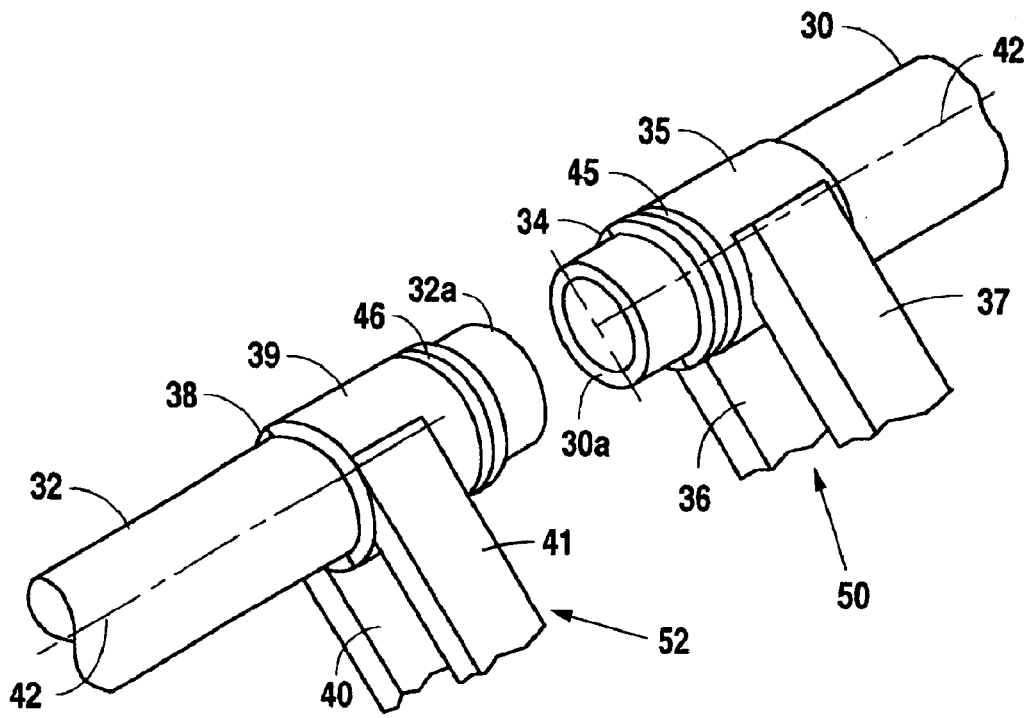
Figure 12:
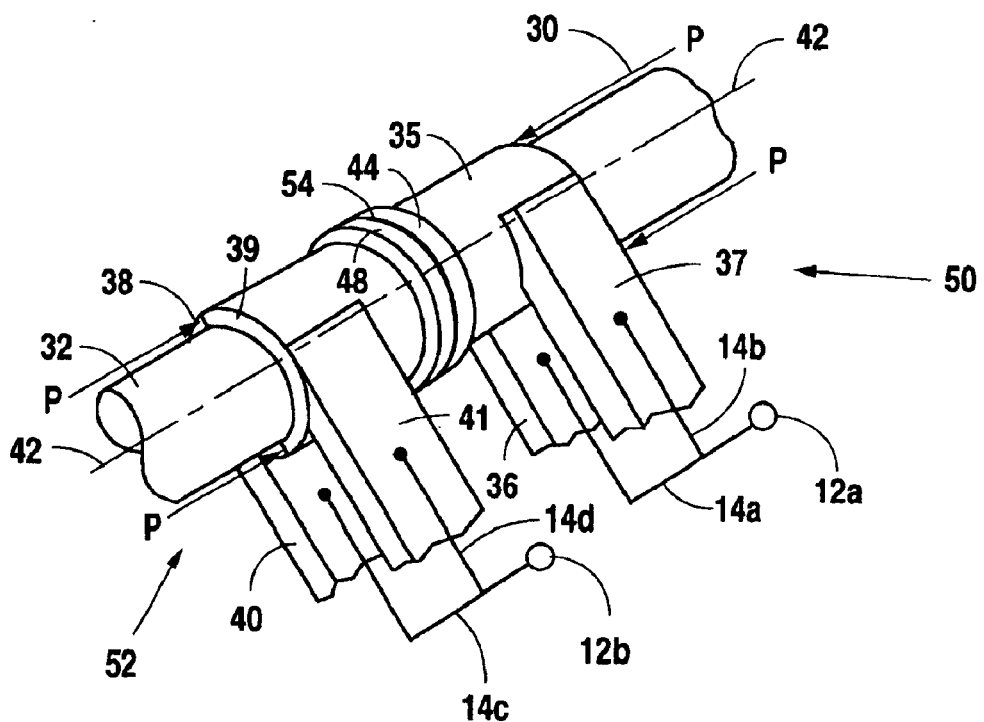

FIGS. 10–12 show a fourth embodiment of the invention which is designed to bond the entire periphery of the hollow tissue, such as a blood vessel, discussed above in connection with FIG. 8. The blood vessel is shown in FIG. 10 after it has been cut into parts 30 and 32. Tissue part 30 is inserted into semicircular electrode sleeve 34 attached to the end of arm 36. Similarly, tissue part 32 is inserted into semicircular electrode sleeve 38 attached to the end of arm 40. The axes of sleeves 34 and 38 are aligned along line 42, and tissue ends 30*a* and 32*a* face each other. As shown in FIG. 11, another semicircular electrode sleeve 35 is placed onto its mate 34 to encircle tissue part 30 therebetween. Electrode 35 is attached to the end of arm 37. Likewise, semicircular electrode sleeve 39 is placed onto its mate 38 to enclose tissue part 32 therebetween. Electrode 39 is attached to the end of arm 41. These various parts can be part of a tool (not shown), the details of which are apparent to one with ordinary skill in the art based on the explanations and descriptions provided herein.

Tissue end 30*a* is folded back on itself by turning it inside out with pincers to form flange 44. The flange 44 is pulled up over electrodes 34, 35 to be tight against the ends of the electrodes. Also, in order for tissue part 30 to be secured onto the electrodes, a peripheral collar 45 (FIG. 11) is formed onto which the edge of end 30a is placed. In similar fashion, electrodes 38 and 39 have peripheral collar 46 formed therein. End 32a is pulled tightly over collar 46 to form flange 48.

As shown in FIG. 12, output terminals 12a and 12b of the power source are connected to the above-described arrangement. More specifically, current from terminal 12a is provided via conduction wires 14a and 14b and arms 36, 37 to electrodes 34, 35 respectively. Of course, current could be supplied directly to the electrodes by attaching wires 14a and 14b thereto. Current is provided in like fashion to electrodes 38 and 39, respectively, via wires 14c and 14d, and arms 40 and 41.

Assembly 50 for holding tissue part 30 and assembly 52 for holding tissue part 32 are at the tips of pincers or forceps (not shown), and these are brought toward each other by moving one or both along line 42 in order to compress flanges 44 and 48 along the entire periphery formed by the electrodes 34, 35, 38 and 39. Pressure and current are applied in the same manner as described above with respect to FIGS. 1–5, and the result is a circular seam 54 produced by a single thermal cycle. After the bond is formed, flanges 44 and 48 are removed with pincers from the electrodes. The electrode mates are then separated to release the now re-joined hollow tissue parts 30 and 32.

The periodic variation (i.e. modulation) of the heat intensity generated in the tissue promotes the creation of a bond. Sharp temperature rises separated by intervals increase the duration of the tissue being exposed to a stressed state which should promote the rupture of the cellular membranes (why this is relevant is explained below) and aids in formation of a solid bond. Also, the modulation of heat with application of a constant average power results in an increase of the time that the internal tissue layers i.e. between but spaced from electrodes 11, are exposed to a high temperature. Not only the temperature exceeding a certain limit but also the duration of tissue exposure to that temperature are important for the coagulation process with energy absorption needed to form a bond. In this connection, modulation of heat with application of a constant average power leads to a positive result. In order to explain this assertion, consider a "temperature pulse" variation in a linear approximation with repeated short-duration, or pulsed, heating of (or energy release into) tissue is applied.

$$Q = \int_0^T \theta dt$$

where
Q is pulse
t is time,
T is duration of time during which current is passed through the tissue, and
Θ is temperature.

The calculations show that temperature increase is effective for a larger part of the tissue volume between the electrodes when pulsed heating is applied in comparison with when continuous heating is applied. Heat conduction in the electrode affects the heating of the layers immediately adjacent to the electrode. Let us assume that the tissue heating is pulsed with N cycles (e.g. N=4 in FIG. 13), each cycle having a time duration τ. High frequency current passes through the tissue during time $t_u$ in every such cycle of duration τ. The volume power of heat generated is q. Let us compare tissue heating under these pulsed mode conditions with continuous mode tissue heating at per-volume power $q_o$. The average volume power in the pulsed heating of tissue is $q_o$, the same as in the continuous mode, i.e.

$$q \cdot t_u \cdot N = q_o \cdot T$$

where:

$$q = q_o \frac{T}{t_u N} = q_o \frac{\tau}{t_u}$$

Figure 13:
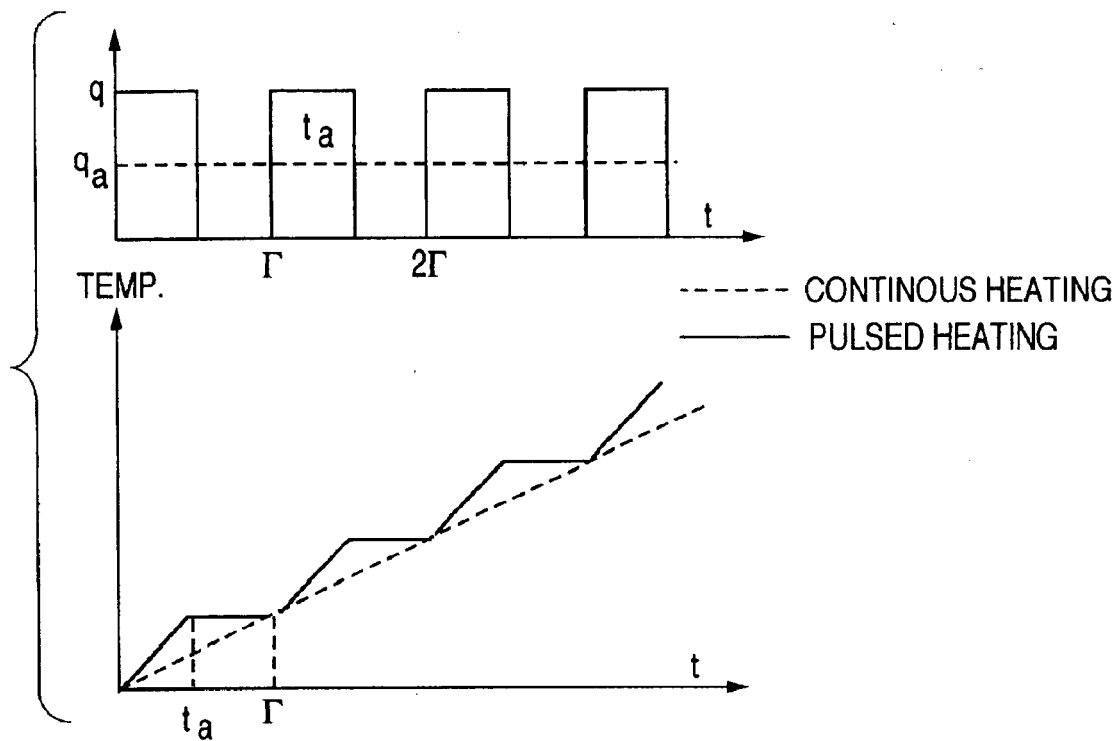
FIG. 13 shows a plot of volume power of heat release q at the tissue/tissue interface as a function of time, and of temperature as a function of time for comparing continuous mode and pulsed mode of heat release, when the mean value of $q_o$ applies to both modes.

As shown in FIG. 13, in the continuous mode, tissue temperature increases in proportion to the time duration that current is applied, as per $$\theta = \frac{q_o T}{c\gamma}$$

where c is heat capacity, and
γ is density.

In the pulsed mode, the tissue temperature also increases as the high frequency current flows during time $t_u$, but the increase occurs at a steeper rate since $q > q_o$. During the time of no current flow, the temperature remains constant until the beginning of the next heating cycle due to low conductivity of tissue (FIG. 13). By the end of the heating process in the continuous mode "temperature pulse", $$Q_H = q_o T^2/c\gamma$$

whereas in the pulsed mode:

$$Q_n = \frac{T^2}{c\gamma}\left[1 + \frac{1 - \frac{t_u}{\tau}}{N}\right]$$

Figure 14:
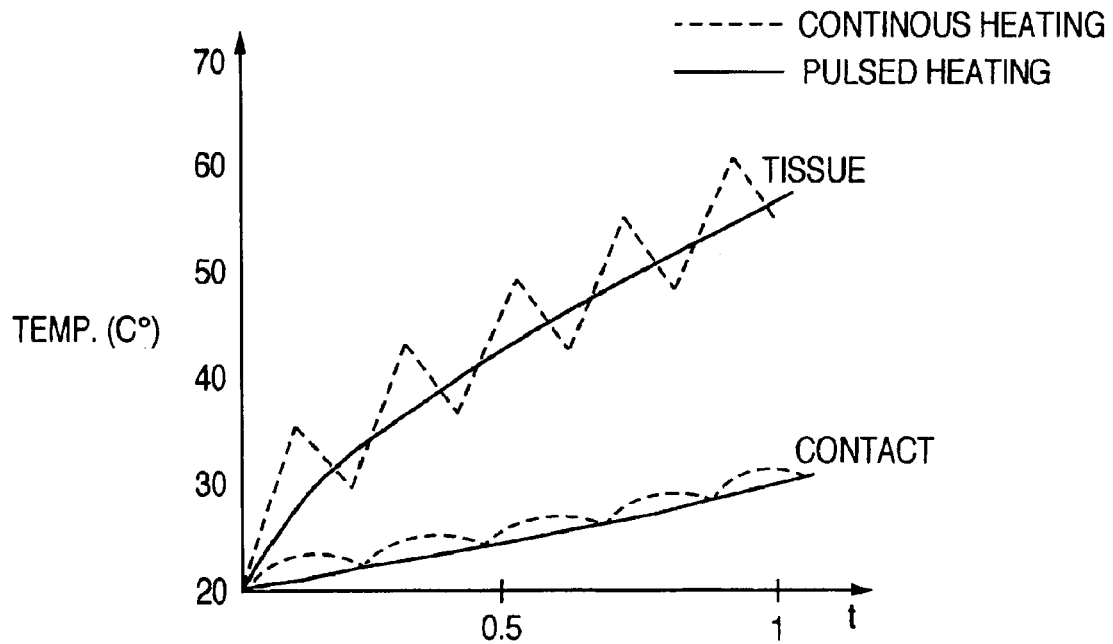
FIG. 14 shows plots of temperature as a function of time at the contact interface between an electrode and tissue ("contact" curve), and also at a distance of 0.01 cm from such contact interface ("tissue" curve) for continuous mode heating and pulsed mode heating.

The difference $$Q_n - Q_H = \frac{q_0 T^2}{c\gamma} \cdot \frac{1 - \frac{t_u}{\tau}}{N}$$

produces an additional effect as to tissue bonding. Moreover, the temperature at the electrode-tissue contact surfaces remains practically the same for both modes (FIG. 14).

It follows from the above that in the pulsed mode the required bonding can be achieved at lower per-volume power than in the continuous mode, and consequently at a lower temperature in the electrode-tissue contact zone. The tissue adhesion to the electrodes will thus be lower. This is one advantage of using the pulsed mode heating.

It follows from the above formula for $Q_n - Q_H$ that the lower is $t_u/\tau$, the higher must be q (see FIG. 13) to maintain the same $q_o$, and the longer is the time duration that tissue remains under the increased temperature conditions. There must be optimal values for $t_u/\tau$ and N. Values of $t_u/\tau = 0.5$ and $4 \leq N \leq 6$ were used to provide high frequency current modulated with square pulses of lower frequency (4 to 6 Hz). The obtained experimental results were positive.

The purpose of low frequency pulse modulation is explained succinctly as follows. Initially, it may seem that during the break in current flow (i.e. during $\tau - t_u$) the temperature in the tissue/tissue contact area should decrease and, therefore, the probability of a good bond will be reduced. Actually, the effect of low frequency modulation results in increased exposure of tissue to high temperature treatment because the tissue at the tissue/tissue interface receives the increased energy generated by the HF current as well as retaining the heat for a longer time because it is relatively distant from the heat sink effect of the electrodes. Thus, the low frequency modulation effect is explained by a longer duration of tissue exposure to high temperature which allows a decrease in the total energy needed for forming the bond and consequently reduces the adhesion of tissue to the electrodes. An increase in the modulation frequency (i.e. the value of N) reduces this effect to zero.

Peculiarities of Tissue as an Element of an Electrical Circuit

Any biological tissue includes cells and inter-cellular fluid. The latter contains a small quantity of albumin, most of it concentrated in protoplasm. The cells and inter-cellular fluid are separated with high electrical resistance membranes. The current conductivity properties of tissue at low voltage are caused mainly by motion of inter-cellular fluid ions. In an alternating electric field, ions and polar molecules of protoplasm contribute to conductivity properties. The AC current caused by periodic alignment of dipoles induced by the alternating electric field is called a bias current. The higher is the frequency, the higher is the bias current in the membranes and correspondingly in protoplasm.

The generation of a monolithic connection bonding together the tissue edges may only be possible due to, firstly, rupture of cellular membranes and, secondly, coalescence of cellular protoplasm. The rupture of the cellular membranes due to current flow therethrough is a gradual process although it has a somewhat chain-reaction-like character. Such rupture can also be accomplished with tissue deformation caused by pressure applied to the tissue with the electrodes.

An electrical rupture of a cellular membrane can occur by exposure to heating, but only under the condition of certain combinations of electric field voltage and temperature. The electrical rupture starts with the cells having the weakest membranes. The electric field voltage drops in the cells with ruptured membranes due to decreased resistance therein, and voltage correspondingly increases in the cells with as yet unpunctured membranes. The rupture probability of the neighboring cells thus increases, and so on.

Such a phenomenon of tissue resistivity decrease due to rupture of the cellular membranes is corroborated by measurements. It is characteristic that the higher the voltage which is applied to the electrodes, the sharper is the resistivity drop. One more circumstance worthy of being pointed out is that an increase of the clamped tissue volume results in delaying the tissue resistivity drop which occurs due to rupture of the cells. A statement that these relationships are precise would not be accurate. Differences in tissue structure also has a significant impact on the process.

As regards use of tissue deformation caused by pressure applied with the electrodes, under such pressure the compressed tissue stretches in the direction perpendicular to the electrode axis. This may cause a purely mechanical rupture of some membranes. After electrical rupture begins, such mechanical rupture becomes more probable.

A constant difference in potential between the electrodes causes tissue deformation to be accompanied by the increase in electrical field strength on membranes that are still intact which, in turn, facilitates rupture of those membranes.

Thus, the initial heating of tissue during the first stage of the thermal cycle serves to create a conductivity path through the tissue to enable current flow with a relatively uniform current density principally confined to the tissue clamped between the electrodes.

Tissue heating during the second stage of the thermal cycle is accompanied by structural changes in the albumin, namely globular molecules straighten out and become intertwined among themselves, which create a decrease in tissue conductivity.

During the second stage it is preferable to increase the clamping force applied by the electrodes for the purpose of creating the best conditions for creating a bond. It has been experimentally proven that an increased force applied on the electrodes in the second stage results at least in 10–20% increased strength of the tissue bond.

After the second stage is completed, it is preferable to continue applying the clamping force to the bonded tissue for a certain time. It is not so much the duration of this additional clamping time that is important but, rather, the sequence of current shut-off after the second stage followed by removal of clamping pressure.

Peculiarities of Frequency Selection

Frequencies selected for electrical surgery purposes in accordance with this invention are in the range of 50 to 2000 kHz. This frequency range is not perceived by the nervous system of humans and animals.

Experiments were conducted within a wide frequency range to test the strength of the bond and determine the dispersion, or variance, of the results. The experiments showed, for example, that 50 kHz is the optimal frequency for bonding an incision in a rat stomach. This frequency provides the strongest bonding and the closest to minimal dispersion. The 50 kHz frequency is well tolerated by a live organism and its use is possible. On the other hand, for a very thin tissue, like the one wrapped around a nerve stem, a frequency of 1000–1400 kHz is more appropriate. It was concluded from these experiments that careful selection of frequency depending on the thickness and type of tissue is required.

Automatic Control

The preferred approach for usage of electrocoagulant bonding in practical surgery is a computerized system. A surgeon will have to input information into a computer, such as the kind of animal, its age, organ to be operated, and tissue type. This data would enable the computer to find in its memory a proper prestored bonding mode close to the optimal (as explained below). There also should be included an optional feature enabling the surgeon to make additional corrections in the bonding mode during surgery, as well as for the computer to make certain adjustments, taking into account specific peculiarities pertinent to certain animals and potential interferences (disturbances) resulting from actual conditions of the surgery.

The following are possible disturbances affecting the bonding process:

a) contamination of working surfaces of electrodes,
   b) variation of the tissue thickness,
   c) variation of the clamping force of electrodes,
   d) by-passing the current through adjacent tissue areas,
   e) inhomogeneity of tissue in the bonded area,
   f) excessive temperature of electrodes,
   g) inhomogeneity of tissue surface, e.g. dry, damp, traces of blood, etc.

The automatic control system which relies on feedback circuits responsive to such disturbances should vary the heating mode in such a manner that their effect is minimized. Contamination of the work surface of the electrodes should be detected in the beginning of the bonding before any serious damage is done. For that purpose, a short duration high frequency probing pulse is fed through the tissue portion 10 for determination of its impedance. Should it be higher than the predetermined level for the type of tissue being bonded, the surgeon needs to be so informed by a signal so that the surgical tool is cleaned or replaced.

Shorting of the electrodes through the tissue clamped therebetween may also be detected by a probing pulse. If the impedance measurement is lower than a certain predetermined level, the bonding process should be immediately discontinued and the surgeon notified.

Variation of the tissue thickness can be detected by way of measuring mechanical strain on the forceps cantilevers, or arms, (described below) and comparing it with the distance of the latter's travel. Direct measurements are also possible but they would complicate a simple tool like forceps and are hardly acceptable. As has already been pointed out, the tissue thickness affects the rate of impedance drop to its minimal value, provided all other factors remain unchanged. This factor is used for computerized control of the bonding process (as explained below).

Disturbances caused by previously bonded spots adjacent the zone 7 being bonded are not so significant, provided the voltage fed to the electrodes 11 has been held constant. Shunting of the tool's current through other tissue parts should be prevented by way of reliable insulation covering all surfaces of materials that conduct electricity, except the work surface of the electrodes. It is more difficult to create a control system responding to the (e) type of disturbance. The change of tissue impedance caused by its inhomogeneity may not require a change of power or energy for bonding. In this case, indications indirectly reflecting the bonding process should be sought after, as discussed below.

Overheating of the electrodes can be eliminated by way of having made provisions in the computer program for limiting the amount of time and the rate of tool operation. This is done by generating an audible and/or visual alarm signal which notifies the surgeon that the tool needs cooling off.

The tissue surface condition (g) should be initially checked and then monitored by the surgeon. Nonetheless, effects of these disturbances should be at least partially monitored by the control system, as pointed out above.

System Without Feedback

This is the most unsophisticated system. The bonding mode is determined by the rate of high frequency voltage rise in the first stage, voltage heating time duration in the second stage and clamping pressure. Each of these values is set up by the operator or recovered from computer memory and applied during the operation.

The system does not respond to any of the above-listed disturbances.

System With Stabilization of the Output High Frequency Voltage

This embodiment differs from the one immediately above by providing a more accurate reproduction of the intended bonding mode despite disturbances (a) through (d). The system should respond to the condition of the electrode work surfaces and to short circuits which arise during the tool's operation cycle, both before the bonding and during tissue heating. The system also informs the operator of its diagnosis results.

As described above, one feature of the invention is to use a two-stage thermal cycle in which during the first stage the voltage increases at a predetermined rate for a certain time, and during the second stage a continuous voltage is applied to the tissue at the maximum voltage level reached in the first stage. As also described above, tissue impedance is used in accordance with another feature of the invention to stop current flow in order to prevent excessive coagulation and resultant tissue damage.

Figure 20:
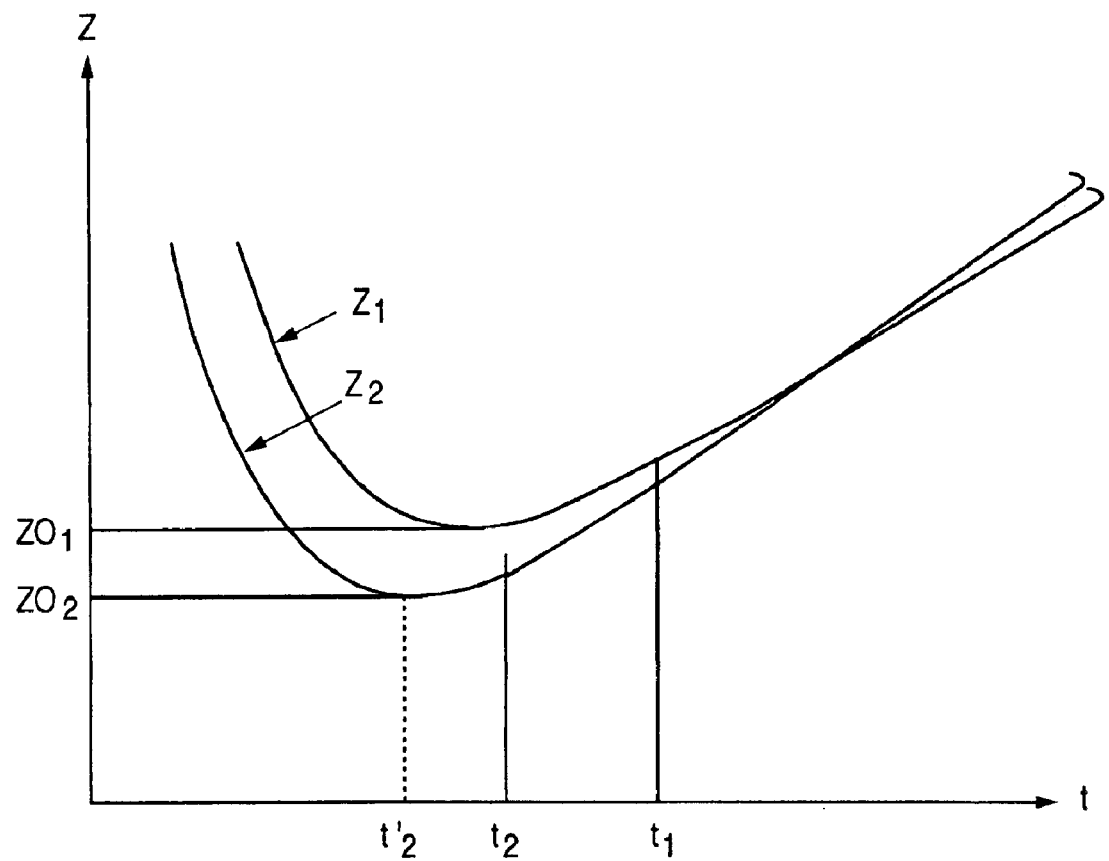
FIG. 20 is a graph of tissue impedance over time for tissue being heated by high frequency current.

These two features are combined as follows. The first stage continues until occurrence of the minimum impedance Zo is determined (see below and FIG. 20). Upon that (i.e. at time $t_2$ for impedance curve $Z_2$) further rise of the voltage is halted and the voltage level which has been reached is stabilized for use in the second stage. The second stage is then applied until the preset value of Z/Zo (see below) is reached (e.g. at time $t_2$), at which time further current flow is stopped.

Automatic Control System Employing Relative Value of Tissue Impedance

As explained above in connection with the article authored by Vallfors and Bergdahl, prior art techniques rely on determining absolute values of impedance Z or of its change with time dZ/dt and their use for automatic control with feedback. However, these values can vary greatly from tissue to tissue because impedance is affected by many variables. If these prior art techniques are restricted to the same type of tissue, such as blood vessels, they can be valuable. However, significant inaccuracies, and resultant tissue damage, can occur when values predetermined for one type of tissue are applied to control current flow through another type of tissue.

Accordingly, the invention utilizes relative values based on the rate of Z/Zo, where Zo is the minimum impedance value determined each time bonding is performed on a particular type of tissue, and Z is the present value of impedance being measured as current is applied to such type of tissue. Thus, the minimum point $Zo_1$ on the impedance curve $Z_1$ (FIG. 20) is calculated by well known means e.g. utilizing computer 70 described below. When the ratio $Z/Zo_1$ reaches a preset value, further heating is stopped by breaking the current flow, e.g. at time $t_1$. For the next bonding process on another type of tissue, impedance curve $Z_2$ is processed in the same way with the result that current flow is stopped at time $t_2$. The use of this approach is advisable in combination with the embodiment which provides stabilization of a high frequency output voltage (see below).

System With Automatic Setting of High Frequency Voltage

This system responds to the (b) type of disturbance which is caused by variation of the tissue thickness. As has been pointed out above, a current conducting path is created in the clamped flange of tissue by way of the rupturing cellular membranes. An increase in tissue thickness results in a longer time being required for the formation of a current conducting channel, and vice versa. If in the first stage of the thermal cycle the high frequency voltage is increased at the rate of approximately 300–400 V/sec, the tissue impedance will drop smoothly until it reaches a certain minimal value Zo. As soon as the minimum value of tissue impedance Zo is reached, the high frequency voltage becomes stabilized at the particular level which has been reached. That voltage level is then applied in the second stage.

Thus, the increase and decrease in tissue thickness causes the voltage to be set at higher values and at lower values, respectively, for the second stage.

Current cutoff to stop the tissue heating is achieved by the control system in response to the relative value of tissue impedance Z/Zo, as explained above.

It is important to select the correct rate of voltage rise. For example, it has been noticed that for stomach and intestinal tissues, a rate of voltage rise exceeding 400 V/sec is not advisable due to an excessively fast formation of the conductive path. The system must provide monitoring to inform the surgeon about the correspondence between actual voltage parameters and the voltage parameters preset in the computer.

Circuitry for Electrical High Frequency Bonding

Figure 15:
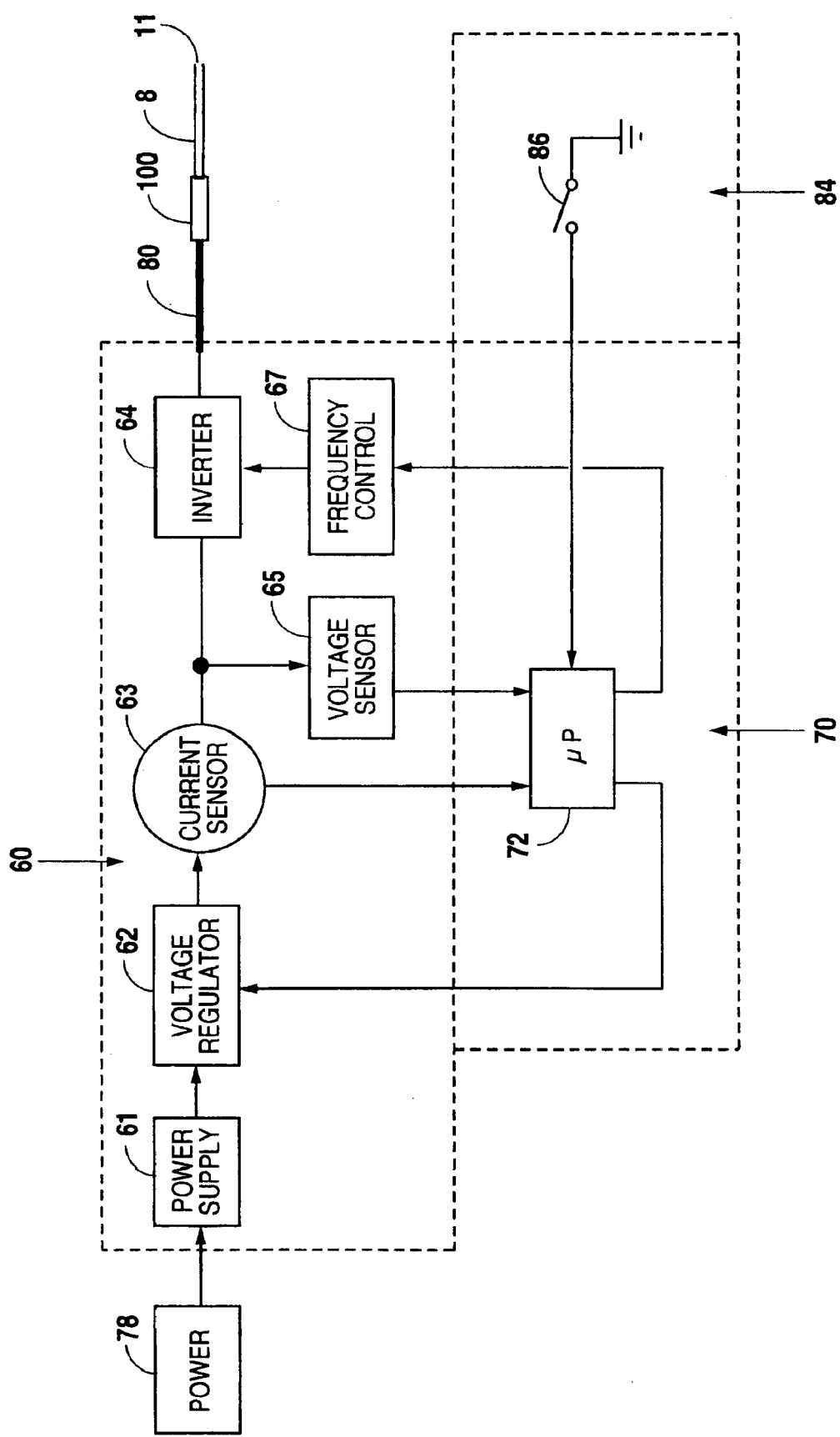
FIG. 15 is a schematic block diagram of a circuit for providing a high frequency electrical signal to the electrodes in accordance with the invention.

FIG. 15 shows the circuitry which produces the high frequency signal provided to the electrodes 11.

Signal generator 60 converts AC mains voltage from power source 78 to the signal which is provided to electrodes 11 via cable 80 and arms 8 which are mounted in sleeve 100. Power supply 61 receives the AC mains voltage and provides a regulated, isolated, filtered DC voltage of 100 volts. Voltage regulator 62 receives the output of power supply 61 and provides an output voltage that can be controlled to any level between 0 and 100 volts. Inverter 64 transforms the DC voltage it receives from voltage regulator 62 to an alternating signal with a controlled frequency. The output of inverter 64 is coupled to electrodes 11.

Current sensor 63 and voltage sensor 65 measure the current and voltage, respectively, at the output of voltage regulator 62, and these measurements are provided to computer control system 70. Computer control system 70 includes a suitable microprocessor 72 operating in conjunction with other standard and well known system components (not shown) which are required to perform the specified functions for implementing the present invention, such as memory devices, interface circuits, D/A and A/D circuits, keyboard, display, speaker and so on.

Signal generator 60 also includes a frequency control circuit 67 which provides an output signal to inverter 64 for controlling the frequency of the signal provided to electrodes 11.

Footpedal 84 is provided with a switch 86 which is positioned to be actuated by the surgeon. By closing switch 86 the surgeon commands the circuitry to commence a thermal cycle for bonding tissue.

The circuitry depicted in FIG. 15 can perform all of the various tasks described above for tissue bonding in accordance with the invention. As explained above, implementation of the invention requires the circuitry to operate in accordance with certain voltage, current and impedance values. More specifically, as explained above, the voltage on electrodes 11 rises at a predetermined rate during the first stage of the thermal cycle. This voltage increase is commanded by computer control system 70 ("computer") via an output from microprocessor 72 coupled to voltage regulator 62. Voltage sensor 65 measures the voltage level provided by voltage regulator 62, and provides it as feedback to microprocessor 72. If a discrepancy exists between the commanded voltage and the measured voltage, a suitable correction is made under computer control.

Thus, computer 70 controls the voltage and duration of the first stage. Operation of an analogous nature is provided to carry out the second stage in terms of controlling voltage and duration.

Current sensor 63 provides an instantaneous current measurement to computer 70. Since the voltage on electrodes 11 is computer controlled, the current level is based on the tissue impedance. Thus, the tissue impedance can be calculated from the ratio of voltage to current. In this way the computer 70 determines Z and Zo. These parameters are used by computer 70, in accordance with the description provided above, to control the thermal cycle.

The frequency of the HF signal provided to electrodes 11 is also controlled by computer 70. The required frequency is outputted by microprocessor 72 and applied to frequency control circuit 67 which determines the frequency generated by inverter 64.

The low frequency modulating signal is produced at the output of power supply 61 in accordance with voltage control signals generated by computer 70.

All of the components shown as blocks in FIG. 15 are well known. Obtaining such components and arranging them to operate with each other in the manner described in detail herein is obvious to anyone with ordinary skill in the art. Likewise, programming computer 70 to operate in the manner described herein is obvious to anyone with ordinary skill in the art.

As to computer 70, in its memory are stored the voltage, voltage increase rate, frequency and other parameters predetermined by experimentation to be effective to bond tissue of a particular thickness and structure. The computer memory must contain data about bonding modes for the tissues of various organs depending on the type of animal and its age. Examples of data stored in memory are set forth below in Table 1.

TABLE I

| animal organ | tissue thickness compressed (approx.) microns) | electrode work surface semi-sleeve electrode (microns) | clamping force (N) | voltage rise rate (V/sec) | voltage (V) | frequency (kHz) | modulation frequency (Hz) | two stage thermal cycle (time msec) |
|---|---|---|---|---|---|---|---|---|
| Method 1 rat abdominal aorta | 110 ± 20 | 350 ± 50; dia 1550 | 2.6 | 213 | 50 | 1000 | | 150 + 1200 = 1350 |
| Method 2 rat abdominal aorta | 110 ± 20 | 350 ± 50; dia 1550 | 1.5 | 213 | 32 | 1000 | 0 | 150 + 400 = 550 |
| rat epineurium | 25 ± 5 | 400 × 500 | 0.35 | 2207 | 34 | 1000 | 0 | 15 + 50 = 65 |
| rabbit artery + vein, | 50 + 25 = 75 | 350; dia 1550 | 1.5 | 200 | 30 | 1000 | 0 | 150 |
| Method 2 rabbit large intestine | 700 | 1 × 2 mm | 3.5 start 5.0 end | 300 | (1)45 | 50 | 6.0 | 150 + 1200 |
| | 700 | 1 × 2 mm | 3.5 start 5.0 end | 267 | (2)40 | 50 | 6.0 | 150 + 1400 |

TABLE I-continued

| animal organ | tissue thickness compressed (approx.) microns) | electrode work surface semi-sleeve electrode (microns) | clamping force (N) | voltage rise rate (V/sec) | voltage (V) | frequency (kHz) | modulation frequency (Hz) | two stage thermal cycle (time msec) |
|---|---|---|---|---|---|---|---|---|
| rabbit liver | 2.5 to 0 | 1 × 3 mm | 4.5 | 200 | 30 | 50 | 6.0 | 150 + 1200 |
| rabbit gall bladder | 300 ± 50 | 0.5 × 2 mm | 3.0 | 200 | 30 | 50 | 60 | 150 + 1200 |

(1) serous-serous seam
(2) mucous-muscle seam

Computer 70 must be provided with information to identify, for example, the tissue type. Thus, the keyboard (not shown) can be used to enter "rabbit liver". Other input data regarding tissue thickness, electrode work surface and clamping force is entered manually and/or automatically by suitable devices. Once all of the input data has been entered, computer 70 will generate corresponding output data to perform the thermal cycle, such as the voltage rise rate for the first stage, the voltage for the second stage, the high frequency, the modulation frequency, the duration of both stages (in some embodiments), and so on.

The input data about the tissue which requires bonding is entered into the computer control system 70, output data is retrieved, and the thermal cycle commences at the surgeon's command. The output data can be automatically corrected in correspondence with a control algorithm based on feedback signals. Alternatively, system operation based on the output data retrieved from computer 70 can be corrected manually by the surgeon's override according to the results he observes from the first thermal bonding cycle.

Tools

The electrodes 11 must not only deliver current to the tissue, but to cool off its surface as well. Based on calculations and experiments, it has been determined that the electrodes must be made of metal with a high heat conductivity. As between copper and stainless steel, for example, a temperature rise of 10° C. was measured immediately at the moment of bonding discontinuation at the electrode/tissue interface for copper electrodes (heat conductivity 3.93 W/cm C), whereas for stainless steel the rise was 25° C. (heat conductivity 0.162 W/cm C).

The volume of the electrode defines its heat capacity and, thus, its ability to function effectively as a heat sink and withstand several successive bonding cycles without becoming overheated. The electrode volume Ve should be significantly larger than the volume of the tissue to be bonded. This is expressed by $$Ve \approx CS_e \delta,$$

where $S_e$ is the area of electrode work surface, $\delta$ is the thickness of flange 10, and C is between 5 and 10.

The area size $S_e$ of the electrode work surface is that portion which engages the tissue flange 10, and it defines the current distribution in the tissue contacted between the electrodes 11 and, hence, the distribution of heat generated by current flow within the tissue.

A demonstration of the electrode heat sink effect is depicted in FIGS. 13 and 14.

In FIG. 13 the temperature plotted is deep within the tissue, i.e. at the tissue/tissue boundary. It is assumed that the tissue has poor heat conductivity and, therefore, for the short time between pulses of power essentially no heat energy is lost. Therefore, the temperature will remain nearly constant.

However, FIG. 14 plots two temperatures, namely in tissue very close to the electrode (0.01 cm) and in tissue that is in contact with the electrode. It is shown by the temperature drop between pulses that the electrode conducts heat away rapidly, even during that short time period. Therefore, in the pulsed case for both tissue in contact with the electrode and tissue only 0.01 cm away, the temperature will significantly drop even in the short time between pulses.

It has been discovered that another factor having a significant effect on the heat generated in the tissue and the electrode/tissue interface is the uniformity which is maintained in the area of electrode/tissue contact. The term "uniformity" in this context is defined as being applicable to the nature of the contact (i.e. surface as opposed to point-by-point), perimeter of contact area, and the current density distribution. Such uniformity is maintained by suitable design of the electrodes. In particular, the electrodes are shaped to form a contact area in accordance with a selected ratio between the linear dimension of the contact area to thickness of the tissue. If the ratio is low and the deformation of the bonded material is comparatively low, the area of the highest heat generation is displaced toward the electrode where the current density is the highest, whereas at the tissue/tissue interface the current density is lower. Therefore, bonding starts in the wrong place (i.e. at the electrode/tissue interface) and only later shifts over to the tissue/tissue interface where the anastomosis should be formed. The zone of the initial formation of coagulation overheats, and that causes sticking and has a negative influence on the tissue healing process.

If the tissue deformation, or compression, is rather deep, the current density at the tissue/tissue interface is higher and coagulation forms without zones of high "overcoagulation".

In case of deep tissue deformation (approximately 50%) the ratio of the above-mentioned length dimension of the electrode to the thickness of the tissue layer should be not less than one. In the extreme case of low deformation (very hard tissue) this ratio must reach 3.

Figure 16:
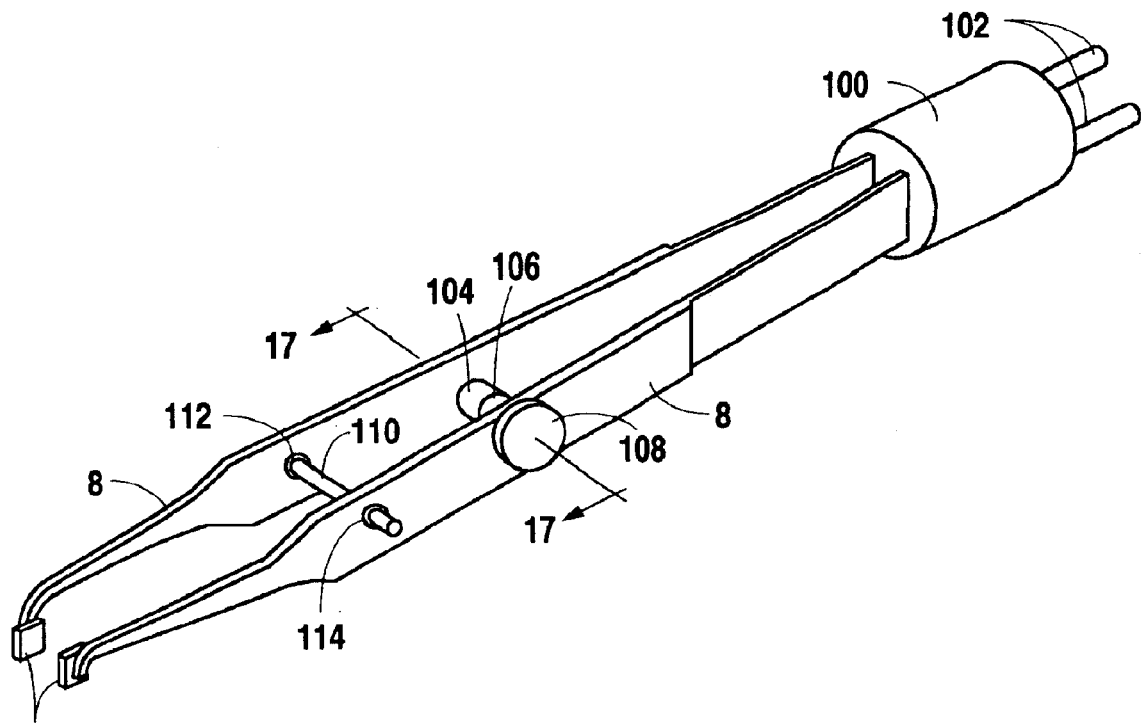
FIG. 16 is a perspective view of a forceps tool for performing bonding in accordance with the present invention.
Figure 17:
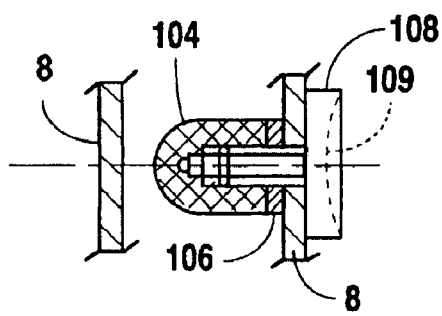
FIG. 17 shows a-cross-section taken along line 17—17 of FIG. 16.

A tool of such type is shown in FIGS. 16 and 17.

The arms 8 (see FIG. 1) are mounted into sleeve 100 and are connected to contact pins 102 for connection to the HF power source 12. Electrodes 11 are soldered to the arms 8 in opposed relationship. One of arms 8 has a lug 104 on the internal side of the arm. It is possible to limit deformation of arms 8 and thus adjust the clamping force of the electrodes on the tissue by replacing this part 104 with another of a different height.

When electrodes 11 come in contact there remains a gap between lug 104 and the opposite arm 8. Further deformation of the arms under the pressure from the surgeon's fingers is limited by the lug and opposed arm coming in contact. The force of tissue compression by the electrodes which is created during this action is expressed by the equation $$P_1 = aG$$

where a is a gap between lug 105 and the surface of the opposed arm, and

G is a proportionality factor determined by the rigidity of the arms.

Further increase of pressure by the surgeon's fingers will not change the compression force applied by the electrodes. The adjustment of the forceps to the needed force $P_1$ is achieved by replacing part 104 by a similar one but of a different height, or by means of changing the number of adjusting spacers 106 placed under lug 104.

When two thick layers of tissue are being bonded, each having a thickness d, and these are placed between the electrodes, the clamping force becomes $$P_2 = (a + 2dx) \cdot G.$$

where x≈R/L, R is the distance from sleeve 100 to sleeve 104, and L is the length of arm 8 from sleeve 100 to electrodes 11.

The following ratio between the forces may be assumed:

$$\frac{P_2}{P_1} < 1.5,$$

where $$\frac{a + 2dx}{a} < 1.5$$

or $$a > 4dx$$

There is a knob 108 with a recess 109 for the operator's finger on the external side of the arm. A strictly fixed location of the operator's finger relative to the arm is an essential condition for controlling the clamping force on the tissue. A recessed spot for the operator's finger makes manipulation easier, especially with a small size tool.

The main parameters that the tool is to meet are defined by tissue thickness d, bonding area S and specific pressure selected depending on the tissue type arm flexure a>4dx force $P_2 = S \cdot p$ rigidity $$G = \frac{P_2}{a + 2dx}.$$

At a preset rigidity G, backlash is $$A = \frac{P_2}{G} - 2dx.$$

Centralizer bar 110 is mounted into one of arms 8 through an electric-insulating sleeve 112, and its other end enters hole 114 in the other arm 8.

Force $P_2$ is preset by selecting the thickness of adjustment spacers 106.

All the free surfaces of the tool excluding the electrodes work surfaces are covered with electric-insulating coating that prevents puncture at the electrical parameter values expected to be used, plus a reasonable margin of safety.

Figure 18:
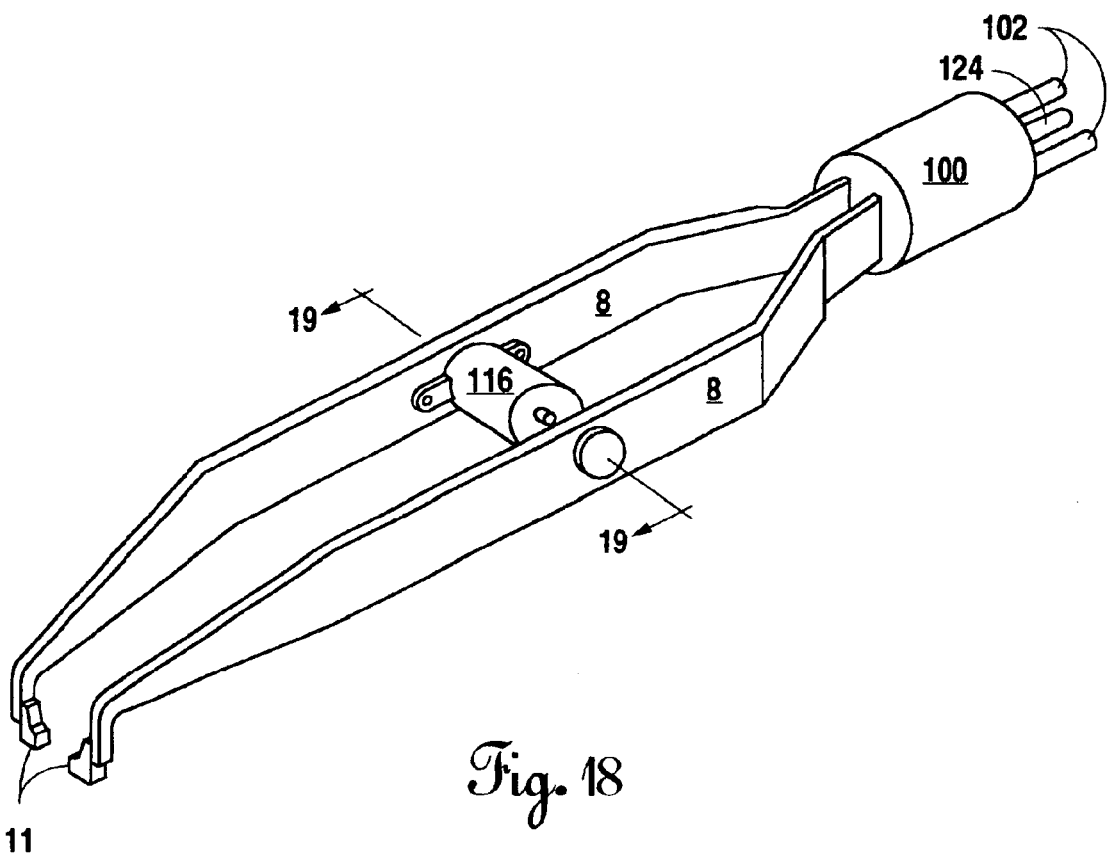
FIG. 18 is an electromagnetic version of the forceps shown in FIG. 16.
Figure 19:
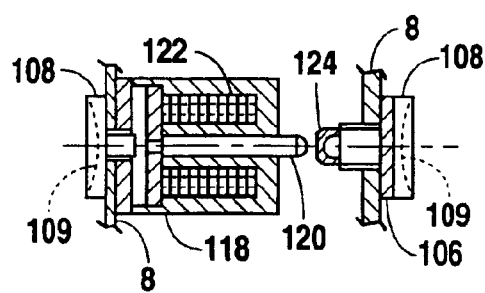
FIG. 19 is a cross-section taken along line 19—19 of FIG. 18.

A tool with two level settings of the clamping force using an electromagnetic drive is depicted in FIGS. 18 and 19. The main principle of this tool is the same as in the one depicted in FIG. 16 in that deformation of arms 8 is limited in order to create the condition for setting the force.

In this case, the deformation is limited not to one certain level but to two selectable levels.

For this purpose, an electromagnet, 116 is mounted on one of the arms 8, its armature 118 is connected with pin 120 that exits through the hole in stator 122.

Before the bonding is initiated the electromagnet is energized, the armature 118 is pulled toward stator 122 and the pin 120 is pulled out to its extended position. During the bonding process a signal to de-energize the electromagnet is sent from computer 78. Armature 118 is released and pin 122 is depressed. The deformation of arms 8 increases under pressure by the surgeon's fingers, providing the required increase of the tissue clamping force. The initial and the final force is preset by selecting the length of pin 120 and lug 124, as well as the number of spacers 106. Stator coil 122 is connected to a DC power source (not shown) through one of the pins 102 through which AC high frequency current flows, and an additional pin 124 mounted into electric insulated sleeve 100. The electric magnet is controlled by computer 78 which controls the main power source 12.

Advantages of the invention have been found to include the following:

the method is simple in usage, requires usual skills in general surgery on stomach, intestine, liver, gall and urine bladders and other organs;

the method is implemented with the help of forceps which is a familiar instrument for surgeons, or with simple devices the usage of which does not require special training;

tissues can be bonded layer-by-layer or in the mass, the welding seam is neat and trim, leak-proof and reliable;

testing of the method on several types of animals (e.g. rabbits, white rats) proved its applicability in layer-by-layer closing of wounds, stomach bonding "end-to-end" and "end-to-side", reconstruction of stomach intactness, gall bladder and urine bladder surgery, and this establishes the wide applicability of the method and possibilities of further extension of its clinical applications;

absence of complications in the post-operational period in 90% of operated-on animals that could be related to the method itself, rather than to improper use of anesthetic or technical errors by the surgeon;

the method reduces the duration of surgery by 50–60%, and facilitates the surgeon's work;

typically, after having tried this method for the first time, surgeons master it without any difficulties and express an inclination to continue deeper study of the method and introduce it into their clinical practice.

The bond in tissue created by this invention has been described herein in terms of the effect on albumin of heat generated by the current passed through the tissue. It has been said that, when suitably heated, the albumin joins the two edges of tissue to each other. This is one possible explanation. However, the physiological changes caused in tissue by the present invention are not yet fully understood. It is possible that physiological changes in addition to or in place of the albumin effect occur due to the invention which contribute to the creation of a bond.

Although specific embodiments of the present invention have been described in detail, various modifications thereto will be readily apparent to anyone with ordinary skill in the art. All such modifications are intended to fall within the scope of the present invention as defined by the following claims.

We claim:

1. A method for bonding soft biological tissue having an incision therein, comprising the steps of:
    gripping a portion of the tissue on both sides of the incision with forceps;
    contacting said tissue portion with electrodes;
    providing a high frequency electrical signal to said electrodes to be passed through said tissue portion;
    monitoring the impedance of the tissue between the electrodes; and
    providing said electrodes with a gradually increasing voltage signal during a tissue preparation stage characterized by decreasing tissue impedance, and then transitioning into another voltage signal during a tissue bonding stage, characterized by increasing tissue impedance, to provide tissue welding that forms a weld to reconnect the tissue;
    wherein a minimum detected impedance value triggers the transition from the first, gradually increasing, voltage signal to the second voltage signal.

2. A method for bonding soft biological tissue having an incision therein, comprising the steps of:
    gripping a portion of the tissue on both sides of the incision with forceps;
    contacting said tissue portion with electrodes;
    providing a high frequency electrical signal to said electrodes to be passed through said tissue portion; and
    applying force with said forceps to compress said tissue portion, said force being set to different levels in two time periods, respectively, while said high frequency electrical signal is being passed through said tissue portion to provide tissue welding that forms a weld to reconnect the tissue.

3. A method for bonding soft biological tissue having an incision therein, comprising the steps of:
    gripping a portion of the tissue on both sides of the incision with forceps;
    contacting said tissue portion with electrodes;
    providing a high frequency electrical signal to said electrodes to be passed through said tissue portion; and
    providing a constant voltage level of said signal during at least a portion of a time period when said high frequency electrical energy is passed through said tissue portion, and modulating said constant level by a fixed, computer-controlled low frequency signal of 60 Hertz or less to provide tissue welding that forms a weld to reconnect the tissue.

4. A method for bonding a flange of soft biological tissue, the flange comprising joined edges of tissue from both sides of an incision, the method comprising the steps of:
    selecting electrodes having a heat conductivity of at least three watts per square centimeter, each electrode having a work surface area and a volume, wherein the volume of each electrode is between five and ten times its work surface area times the thickness of the flange;
    gripping a portion of the tissue on both sides of the incision with forceps operably connected to said electrodes;
    contacting said tissue portion with electrodes; and providing a high frequency electrical signal to said electrodes to be passed through said tissue portion;
    wherein the volume of said electrodes relative to volume of said tissue portion operates as an effective heat sink for conducting heat away from said tissue and thereby prevent sticking of tissue to said electrodes to provide tissue welding that forms a weld to reconnect the tissue.

5. A method for bonding soft biological tissue having an incision therein, comprising the steps of:
    gripping a portion of the tissue on both sides of the incision with forceps;
    contacting said tissue portion with electrodes;
    determining the thickness of the tissue gripped;
    communicating the measured tissue thickness into a control system that controls the rate of power applied to the electrodes, the control system selecting a voltage rise rate appropriate for the measured tissue thickness;
    applying a voltage to said electrodes to be passed through said tissue portion; and
    increasing the voltage at the selected voltage rise rate.

6. The method of claim 5, further comprising monitoring the impedance between the electrodes as a function of time for a minimum impedance level.

7. The method of claim 6, further comprising the step of terminating further increase in the voltage applied to said electrodes upon detection of said minimum impedance value.

8. The method of claim 7, further comprising the step of stopping said electrical signal from being passed through said tissue portion when a value of the monitored impedance signal reaches a preset multiple of said minimum impedance value.

9. A method for bonding soft biological tissue having an incision therein, comprising the steps of:
    gripping a portion of the tissue on both sides of the incision with forceps;
    contacting said tissue portion with electrodes;
    providing a gradually rising voltage to said electrodes for passing electric current through said tissue portion, the rate of the voltage rise being specific for each bonded biological tissue;
    measuring impedance of said tissue portion as a function of time while said voltage is provided to said electrodes;
    determining and storing a minimal value of said impedance;
    stabilizing the high frequency voltage at a level corresponding to said minimal impedance value;
    determining a ratio of said measured tissue portion impedance to said minimal value; and
    stopping said high frequency voltage from being passed through said electrodes when said impedance ratio reaches a preset value, said preset value being specific for each bonded biological tissue to provide tissue welding that forms a weld to reconnect the tissue.

* * * * *